United States Patent [19]

Harper et al.

[11] 4,298,759

[45] Nov. 3, 1981

[54] SEPARATION OF COBALT AND MANGANESE FROM TRIMELLITIC ACID PROCESS RESIDUE BY EXTRACTION, ION EXCHANGER AND MAGNET

[75] Inventors: Jon J. Harper, Naperville; Stephen J. Pietsch, Oak Park, both of Ill.

[73] Assignee: Standard Oil Company (Indiana), Chicago, Ill.

[21] Appl. No.: 218,059

[22] Filed: Dec. 19, 1980

[51] Int. Cl.$^3$ .................. C07C 51/42; B01J 37/00; C01G 45/00; C01G 49/00

[52] U.S. Cl. ..................... 562/485; 252/415; 252/420; 423/49; 423/139; 423/140; 423/151

[58] Field of Search .................. 562/485, 414, 487; 252/415, 420; 423/49, 139, 140, 151

[56] References Cited

U.S. PATENT DOCUMENTS 3,071,614  1/1963  Knobloch .................. 562/485

*Primary Examiner*—Alan Siegel
*Attorney, Agent, or Firm*—Ralph C. Medhurst; William T. McClain; William H. Magidson

[57] ABSTRACT

A unique method of separating cobalt and manganese from residue obtained from the manufacture of trimellitic acid by the oxidation of pseudocumene in the presence of cobalt and manganese as metal oxidation catalysts and from each other without contributing to the problem of solids disposal. Said unique method comprises extracting the residues with water, removing cobalt and mangangese from the extract solution with a cation exchanger thereby producing a metal-free solution of trimellitic acid, regenerating the cation exchanger with a strong inorganic acid, adjusting the pH of the spent regenerating acid to pH of 3 to 4 if iron is present to precipitate it as its hydroxide but at least to pH of 6 while also adding powdered manganese to precipitate metallic cobalt.

4 Claims, No Drawings

SEPARATION OF COBALT AND MANGANESE FROM TRIMELLITIC ACID PROCESS RESIDUE BY EXTRACTION, ION EXCHANGER AND MAGNET

This invention relates to the separation of catalyst metals cobalt and manganese from fluid residue produced during the manufacture of trimellitic acid by the oxidation with a source of molecular oxygen of liquid pseudocumene in the presence of catalysis provided by bromine and cobalt and manganese alone or with cerium as catalyst metals and the removal of substantial trimellitic acid and, if used, reaction solvent. More specifically, the present invention pertains to the separation of said metals from said residue and from each other by dissolving the residue in water, treating the solution with an ion exchanger, leaching of the metals from the ion exchanger, adjusting the pH of the solution to a pH of 6, treating with metallic manganese powder and separating metallic cobalt from ionic manganese with a magnet.

State of the Art

No publication has been found which discloses or suggests the combination of trimellitic acid process residue extraction with water, treating the extract solution with an ion exchanger, regenerating the resin thereby forming a second solution of the ions of cobalt and manganese, precipitating metallic cobalt from the second solution, and separating the precipitate with a magnet thereby effecting a separation of cobalt from ionic manganese still in solution.

It is acknowledged that the removal of metal ions by an ion exchanger and even an acid form of cation ion exchangers has been long known. The regeneration of the acid form of cation exchanger with hydrochloric or sulfuric acid thereby providing a solution of the removed metals as chlorides or sulfates has also been long known. However, the above combination of steps apparently is not known or has not been suggested.

BACKGROUND OF THE INVENTION

It is important to the manufacture of trimellitic acid to have at least the cobalt, the most expensive catalyst metal, recycled to the pseudocumene oxidation. For most catalytic liquid phase oxidations of methylbenzenes to benzene carboxylic acids the use of both cobalt and manganese with an oxidation promoter, especially bromine, is the preferred mode of operation. However, for the best oxidation of pseudocumene and for the decrease of co-production of methyl-substituted phthalic acids as impurities, the manganese component of catalysis is either not added at the start of the reaction when all of the cobalt is added and then manganese's addition is delayed until the oxidation is 50 to 55 percent complete (e.g., 2 to 2.5 moles oxygen consumed per mole of pseudocumene), or a portion of the manganese is added with all of the cobalt and the remainder of the manganese is added stepwise in one or two series-connected oxidation zones. Such scheduled or delayed additions of manganese are reported in U.S. Pat. Nos. 3,491,144 and 3,683,016. It will be noted that the use of cerium as third catalyst has some benefit and it can be added at the beginning or scheduled to be added with the manganese.

Thus to reuse cobalt metal oxidation catalyst, that is, recycle it to the oxidation of pseudocumene, it is necessary to separate it or most of it from manganese after recovering cobalt and manganese from the trimellitic acid process residue.

SUMMARY OF THE INVENTION

We have devised a novel method of recovery of cobalt and manganese from a residue of trimellitic acid manufacture which method is a combination dissolving the residue in water at a final temperature of from 25° C. up to 125° C. by the use of a water to residue weight ratio of from 0.25 to 6, preferably 0.35 to 3 and most preferably a 1:1 weight ratio of water to residue at a final temperature of 100° C. Then either the suspension of insolubles in extract solution or preferably the extract solution is contacted with an acid form of cation exchange. The type of cation exchanger used is not critical. The exchanger is suitably used in parallel beds so that one can be regenerated as the other is taking up the catalyst metals.

After said contact, the ion exchanger is regenerated by treating with a strong inorganic acid such as hydrochloric acid, hydrobromic acid or sulfuric acid. The inorganic acid not only regenerates the ion exchanger by hydrogen ion replacement of the metal on the exchanger but also provies an aqueous solution of the catalyst metals as chlorides, bromides or sulfates. Iron in said salt form can be present when it is in the residue as a result of corrosion of iron-containing elements of processing apparatus.

Thereafter the aqueous organic acid solution at least has its pH adjusted to pH 6, when no iron salt is present, at which time powdered manganese in amount at least chemically equivalent to the cobalt in solution is added to precipitate metalic cobalt.

Preferably, metallic manganese is used in an amount of from 1.2 up to 1.5 chemical equivalents of cobalt in solution. When an iron salt is present in the aqueous inorganic acid solution of cobalt and manganese, such solution first has its pH adjusted to pH 4 to 5 to precipitate iron as ferrous hydoxide and then has its pH adjusted a second time to pH 6 for the cobalt metal precipitation. Powdered manganese is used in the metallic cobalt precipitation because the small particulates of manganese do not have metallic cobalt plated out on them as does occur when a larger form of manganese (e.g., ribbon, wire, thin plates, coarse particles, etc.) is used. Temperature with respect to metallic cobalt formation, replacement of cobaltous ion by manganous ion by dissolving of manganese metal, is only of importance to rate of such dissolving and metallic cobalt formation. Useful rates are obtained at temperatures from 20° C. up to 100° C.

The foregoing pH adjustments can be made by the addition of oxides, hydroxides or carbonates of alkali metals, alkaline earth metals, or ammonia or ammonium hydroxide. The latter two are preferred because they do not increase total metals content.

The suspension of metallic cobalt particles in the pH 6 inorganic solution is passed over a magnetic separator which accumulates the metallic cobalt and permits the solution containing manganese ions to pass through.

The foregoing separated metallic cobalt can be dissolved by an acid, preferably hydrobromic acid, so that the thus recovered and separated cobalt is in the form of cobalt bromide.

The foregoing process provides three useful product streams. The first stream after ion exchange is the oxygen-containing aromatics, both dissolved and undissolved, whose main single component, 40 to 60 weight percent, is trimellitic acid which can be distilled to remove solvent water and water of dehydration, water split out upon formation of 4-carboxyphthalic anhydride from the triacid, and then to remove for recovery a trimellitic anhydride (4-carboxyphthalic anhydride) product. A second stream is an aqueous acidic solution of ions of manganese that can be used as the source of manganese for the pseudocumene oxidation. The third stream is the last formed aqueous solution of cobalt bromide which can be used to provide both the cobalt and bromine for catalysis pseudocumene oxidation.

The following TABLE I provides examples of analyses of residues from the manufacture of trimellitic acid (TMLA) per se or its acid anhydride (TMA). Said analyses do not account for the union of the catalyst metals nor do they account for corrosion metal. Analyses showing a more complete accounting of catalyst and corrosion (Fe) metals are later provided.

TABLE I

CHARACTERIZATION OF RESIDUES FROM THE MANUFACTURE OF TRIMELLITIC ACID AND ANHYDRIDE

| COMPONENT IN WEIGHT % | RESIDUE TMLA | TMA |
|---|---|---|
| Acetic Acid | 1.58 | 0 |
| Phthalic Acids | 12.3 | 1.0 |
| Toluic Acids | 0 | 0 |
| Aldehydes | 0.53 | 1.4 |
| Benzoic Acid | 0.5 | 0 |
| Trimellitic Acid | 38.6 | 65.2[1] |
| OLB Compounds[2] | 4.7 | 1.9 |
| HB Compounds[3] | 0.94 | 0.4 |
| Cobalt | 1.17 | 2.51 |
| Manganese | 0.28 | 0.87 |
| Bromine | 0.94 | 0.15 |

[1] Trimellitic acid anhydride.
[2] "OLB Compounds" are other lower boiling compounds.
[3] "HB Compounds" are higher boiling (higher than trimellitic acid) compounds.

TABLE II

CATALYST AND CORROSION (Fe) METALS CONTENT OF TMA PROCESS RESIDUES

| Co | Fe | Mn | Ce |
|---|---|---|---|
| 1.19 | 0.05 | 0.71 | 0.69 |
| 0.77 | 0.05 | 0.37 | 0.16 |

The following will illustrate the removal of metals by an acid form of ion exchanger at various loadings of residue to ion exchanger on a weight basis. Three residues from trimellitic acid processes each of different total metals contents (each residue from different processes for pseudocumene oxidation). Each residue is extracted at a temperature of 100° C. with water in a weight ratio of water to residue of 1:1 and the slurry of insolubles and extract solution is contacted with a separate bed of the ion exchange resin. Each eluting aqueous solution is sampled and analyzed for metals content. One eluting aqueous solution is analyzed for its bromine content. From such analysis the metal removal effectiveness per unit weight of the ion exchanger can be determined.

TABLE III

METAL REMOVAL EFFECTIVENESS PER UNIT WEIGHT OF RESIN

| Residue Number | Total Metal, wt. % | Br | Co | Fe | Mn | Ce | Ratio Residue to $H_2O$, wt. % |
|---|---|---|---|---|---|---|---|
| I | 4.2 | 1229 | 3 | 3 | 3 | 5 | 0.75:1.0 |
|  |  | 1273 | 7 | 3 | 4 | 5 | 1.5:1.0 |
|  |  | 1251 | 87 | 3 | 51 | 9 | 2.25:1.0 |
|  |  | 1113 | 1041 | 12 | 670 | 106 | 3.0:1.0 |
|  |  | 1193 | 2107 | 18 | 1227 | 169 | 3.75:1.0 |
| II | 2.59 |  | 3 |  | 3 |  | 0.5:1.0 |
|  |  |  | 88 |  | 49 |  | 1.5:1.0 |
|  |  |  | 2300 |  | 1300 |  | 2.5:1.0 |
|  |  |  | 2800 |  | 1500 |  | 3.5:1.0 |
| III | 1.3 |  | 3 |  | 3 |  | 0.5:1.0 |
|  |  |  | 10 |  | 6 |  | 1.5:1.0 |
|  |  |  | 67 |  | 33 |  | 2.5:1.0 |
|  |  |  | 529 |  | 239 |  | 3.5:1.0 |

The following data illustrates the effectiveness of the use of powdered manganese to precipitate cobalt from the aqueous acid solution formed by regenerating the ion exchanger to its acid form by hydrochloric acid.

TABLE IV

|  | Cobalt, g | Manganese, g |
|---|---|---|
| Initial HCl Solution I | 1.47 | 0.16 |
| Powdered Mn Added, gm 2.0002 |  |  |
| Final HCl Solution | 0.19 | 2.73 |
| Initial Solution II | 1.82 | 0.31 |
| Powdered Mn Added, gm 2.5025 |  |  |
| Final HCl Solution | 0.03 | 3.06 |

EXAMPLE 2

The catalyst metals cobalt, manganese and cerium are separated from residue, fluid when made, from the manufacture of trimellitic acid in a continuous flow system in the following manner.

The hot (200° C.) fluid residue at 2.4 kg per hour is mixed with 2.4 kg per hour of water at a temperature of 25° C. The resulting slurry of insolubles suspended in extract solution, cooled to 100° C. by indirect heat exchange, is pumped through one of three beds of sulfonic acid type ion exchange resin. The three beds contain a total of 1.2 kg of such ion exchange resin. The three beds are so arranged that while one bed is taking up metals, the second bed is being regenerated by acid washing and the third bed in a regenerated state is in stand-by state ready to be in service when the metal take-up capacity of the first bed is reached. After such metal take-up capacity is reached by the first bed, it is washed with water and then with 12 kg per hour of hydrochloric acid (37 wt.% HCl) to regenerate the ion exchanger and provide an aqueous solution of catalyst and corrosion metals. The outflow of hydrochloric acid containing the catalyst and corrosion metals passing from the regenerated bed is at the rate of about 16.8 kg/hr. Such outflow hydrochloric acid is contacted in indirect heat exchange with the slurry of insolubles suspended in extract solution whereby 10 kg per hour of constant boiling hydrochloric acid (HCl and water vapor) are driven off, condensed and recycled to regenerate an ion exchange bed. The remaining 2.0 kg of solution contains the catalyst metals as chloride solutes.

The 2.0 kg/hr solution of catalyst metal chlorides includes iron chloride. The iron ions result from corrosion of apparatus elements fabricated from stainless steel. To the 2.0 kg solution of catalyst and corrosion metals there are added 670 grams per hour of aqueous ammonium hydroxide (28 to 30 wt.% NH₃) to increase the solution's pH to between 3 and 4 to precipitate iron as ferrous hydroxide, about 0.026 kg/hr. The suspension of ferrous hydroxide in the pH-adjusted solution of metal chlorides is charged to a solid-liquid separator (centrifuge, filter, etc.) to separate the solution and reject the ferrous hydroxide, about 0.026 kg/hr. The separated solution, 2.644 kg per hour, one gram per hour of ammonium hydroxide added to bring the solution of pH of 6 and 14 grams per hour of powdered manganese are combined to precipitate cobalt as metal particles. The suspension of cobalt metal particles in the solution of manganous chloride is passed over a magnetic separator where, in this case, 10.9 grams cobalt metal particles are collected and 1.22 kg per hour of aqueous solution of manganous and ammonium chlorides are separated.

The 10.9 grams per hour of cobalt metal particles are washed free of aqueous solution of manganous and ammonium chlorides and then mixed with 62 grams per hour of hydrobromic acid (47 wt.% HBr) whereby 72.9 grams of cobalt bromide solution (14.95 wt.% Co) are formed.

The solution, 2.675 kg per hour, of manganous and ammonium chlorides is concentrated to a manganese content of 1.8 wt.% by evaporation of 1.455 kg per hour of water and then used as the manganese source for pseudocumene oxidation as before described.

The effluent from the ion exchange amounts to 4.8 per hour, is essentially metal free and is useful as feed to an evaporation system conducted in one or two series-connected wiped-film evaporators for removal of solvent water and water of dehydration of trimellitic acid to its intramolecular anhydride and evaporation of said anhydride and lower boiling organic impurities from higher boiling impurities. Then by either partial condensation or a combination of total condensation and distillation trimellitic acid anhydride (4-carboxyphthalic anhydride) in an amount of about 0.6 kg per hour can be recovered.

The invention claimed is:

1. A method of separating cobalt and manganese from residue of trimellitic acid manufacture and from each other where such residue is obtained by separating trimellitic acid from the product of oxidizing liquid pseudocumene in the presence of cobalt and manganese as metal oxidation catalyst, which method comprises extracting said residue with water in the water to residue weight ratio of from 0.25:1 to 6:1 at a final temperature of from 25° C. up to 100° C., contacting the extract solution or a suspension of insolubles in the extract solution with an acid form of cation exchanger, separating the resulting solution or suspension from the exchanger, regenerating the exchanger with an aqueous solution of a strong inorganic acid, collecting the spent aqueous acid solution resulting from said regeneration, adjusting the ph of said collected aqueous solution to a pH of at least 6 while also adding powdered manganese metal to precipitate cobalt as a metal and dissolve the manganese metal, passing the manganese-treated pH-adjusted solution containing suspended metallic cobalt over one or more magnets, recovering the cobalt metal-free aqueous solution, washing metallic cobalt from the magnets with hydrochloric or hydrobromic acid, and dissolving the metallic cobalt in the acid wash.

2. The method of claim 1 wherein the weight ratio of residue to water is from 1:1 to 3:1, the cation exchanger is a sulfonic acid-modified resin, the strong inorganic acid is hydrochloric or hydrobromic acid and the alkaline material used for pH adjustment is ammonia or ammonium hydroxide.

3. The method of claim 2 wherein the water extraction is conducted by combining the water at 25° C. with residue at 200° C. and cooling the resulting mixture by indirect heat exchange with the spent aqueous acid to evaporate therefrom a constant boiling mixture.

4. The method of claim 2 wherein the residue also contains iron and cerium, the spent aqueous acid has its pH first adjusted to a pH of 3 to 4 to precipitate iron as its hydroxide and then to a pH of 6 for the addition of powdered manganese and precipitation of metallic cobalt.

* * * * *

UNITED STATES PATENT OFFICE
CERTIFICATE OF CORRECTION

Patent No. 4,298,759      Dated November 3, 1981

Inventor(s) Harper, Jon Jay and Pietsch, Stephen J.

It is certified that error appears in the above-identified patent and that said Letters Patent are hereby corrected as shown below:

Patent reads:

| Col. | Line | | |
|---|---|---|---|
| Abstract | 8 | "mangangese" should be | --manganese-- |
| 2 | 25 | "provies" should be | --provides-- |
| 2 | 34 | "metalic" should be | --metallic-- |
| 4 | 49 | "stand-by" should be | --standby-- |
| 5 | 11 | "of pH" should be | --to pH-- |
| 5 | 30-31 | "4.8 per hour" should be | --4.8 kg per hour-- |
| 6 | 8 | "to" should be | --up to-- |
| 6 | 16 | "ph" should be | --pH-- |

Signed and Sealed this

Ninth Day of March 1982

[SEAL]

Attest:

Attesting Officer

GERALD J. MOSSINGHOFF

Commissioner of Patents and Trademarks